(12) United States Patent
Haam et al.

(10) Patent No.: US 8,916,134 B2
(45) Date of Patent: Dec. 23, 2014

(54) METAL NANOCOMPOSITE, PREPARATION METHOD AND USE THEREOF

(75) Inventors: Seung Joo Haam, Seoul (KR); Sung Baek Seo, Seoul (KR); Jae Moon Yang, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 1443 days.

(21) Appl. No.: 12/171,812

(22) Filed: Jul. 11, 2008

(65) Prior Publication Data

US 2010/0008854 A1   Jan. 14, 2010

(51) Int. Cl.
| | | |
|---|---|---|
| *A61K 49/10* | (2006.01) | |
| *C04B 35/634* | (2006.01) | |
| *A61K 49/18* | (2006.01) | |
| *A61K 47/48* | (2006.01) | |
| *C04B 35/628* | (2006.01) | |
| *A61K 49/00* | (2006.01) | |
| *B82Y 30/00* | (2011.01) | |
| *B22F 1/00* | (2006.01) | |
| *H01F 1/00* | (2006.01) | |
| *C04B 35/632* | (2006.01) | |
| *B82Y 25/00* | (2011.01) | |
| *B82Y 5/00* | (2011.01) | |

(52) U.S. Cl.
CPC ..... *A61K 49/1839* (2013.01); *C04B 2235/3279* (2013.01); *C04B 2235/3284* (2013.01); *C04B 2235/763* (2013.01); *C04B 35/634* (2013.01); *A61K 47/48861* (2013.01); *C04B 2235/3262* (2013.01); *C04B 35/628* (2013.01); *A61K 49/0043* (2013.01); *C22C 2202/02* (2013.01); *C04B 2235/3241* (2013.01); *A61K 49/0002* (2013.01); *C04B 2235/3275* (2013.01); *B82Y 30/00* (2013.01); *A61K 49/0041* (2013.01); *B22F 1/0062* (2013.01); *A61K 49/0054* (2013.01); *A61K 49/0093* (2013.01); *A61K 49/1887* (2013.01); *H01F 1/0045* (2013.01); *B22F 2998/00* (2013.01); *C04B 35/632* (2013.01); *C04B 2235/3224* (2013.01); *C04B 2235/3272* (2013.01); *B82Y 25/00* (2013.01); *B82Y 5/00* (2013.01); *B22F 1/0018* (2013.01)
USPC ................................................ 424/9.322

(58) Field of Classification Search
None
See application file for complete search history.

(56) References Cited

U.S. PATENT DOCUMENTS

| | | | | |
|---|---|---|---|---|
| 5,900,228 | A * | 5/1999 | Meade et al. | 424/9.363 |
| 6,740,336 | B2 * | 5/2004 | Trubetskoy et al. | 424/450 |
| 2005/0260137 | A1 * | 11/2005 | Acar et al. | 424/9.34 |
| 2005/0265922 | A1 * | 12/2005 | Nie et al. | 424/1.11 |
| 2006/0204445 | A1 * | 9/2006 | Atala et al. | 424/9.36 |

FOREIGN PATENT DOCUMENTS

KR   10-2007-0088388   8/2007

OTHER PUBLICATIONS

Park S, Healy KE. Nanoparticulate DNA packaging using terpolymers of poly(lysine-g-(lactide-b-ethylene glycol)). 2003 Bioconjug. Chem. 14: 311-319.*
Silver J, Ou W. Photoactivation of quantum dot fluorescence following endocytosis. 2005 Nano Lett. 5: 1445-1449.*
Seo et al. Nanohybrids via a polycation-based nanoemulsion method for dual-mode detection of human mesenchymal stem cells. 2008 J. Mater. Chem. 18: 4402-4407. Published online Jul. 3, 2008.*
Farokhzad et al. Nanoparticle-aptamer bioconjugates for cancer targeting. 2006 Expert Opin. Drug Deliv. 3: 311-324. Review.*
Korean Office Action issued for 10-2008-0069850 mailed May 31, 2010, (English Translation only provided, for pp. 2-4).
Su, Chia-Hao et al., "Nanoshell Magnetic Resonance Imaging Contrast Agents," J. Am. Chem. Soc., 2007, vol. 129, pp. 2139-2146.
Chan, et al., "Quantum Dot Bioconjugates for Ultrasensitive Nonisotopic Detection," Science, vol. 281, pp. 2016-2018, Sep. 25, 1998.
De Palma, et al., "Silane Ligand Exchange to Make Hydrophobic Superparamagnetic Nanoparticles Water-Dispersible," Chem. Mater., vol. 19, No. 7, pp. 1821-1831 and 5 pages of supporting information, Feb. 28, 2007.
Dubois, et al., "A Versatile Strategy for Quantum Dot Ligand Exchange," vol. 129, No. 3, pp. 482-483, Dec. 23, 2006—, J. Am. Chem. Soc.
Fan, et al., "Self-Assembly of Ordered, Robust, Three-Dimensional Gold Nanocrystal/Silica Arrays," Science, vol. 304, pp. 567-571, Apr. 23, 2004.
Ito, et al., "A new methodology of mesenchymal stem cell expansion using magnetic nanoparticles," Biochemical Engineering Journal, vol. 20, pp. 119-125, Aug. 15, 2004.
Kim, et al., "Super-Stable, High-Quality $Fe_3O_4$ Dendron-Nanocrystals Dispersible in Both Organic and Aqueous Solutions," Advanced Materials, vol. 17, pp. 1429-1432, Jun. 2005.
Pellegrino, et al., "Hydrophobic Nanocrystals Coated with an Amphiphilic Polymer Shell: A General Route to Water Soluble Nanocrystals," Nano Letters, vol. 4, No. 4, pp. 703-707, Mar. 26, 2004.
Sehgal, et al., "Precipitation-Redispersion of Cerium Oxide Nanoparticles with Poly(Acrylic Acid): Towards Stable Dispersions," Langmuir The Acs Journal of Surfaces and Colloids, vol. 21, Issue 20, 6 pages, 2005.

(Continued)

*Primary Examiner* — Michael G Hartley
*Assistant Examiner* — Jennifer Lamberski
(74) *Attorney, Agent, or Firm* — Foley & Lardner LLP

(57) ABSTRACT

The disclosure provides metal nanocomposites including one or more metal nanoparticles having a hydrophobic surface and at least partially enclosed by cationic and hydrophilic polymers. The metal nanocomposites are useful as among others, a contrast agent, a diagnostic composition or a pharmaceutical composition.

30 Claims, 7 Drawing Sheets

(56) References Cited

OTHER PUBLICATIONS

Song, et al., "Surface Modulation of Magnetic Nanocrystals in the Development of Highly Efficient Magnetic Resonance Probes for Intracellular Labeling," J. Am. Chem. Soc., vol. 127, No. 28, 2 pages, 2005.

Wang, et al., "A general strategy for nanocrystal synthesis," vol. 437, pp. 121-124, Sep. 1, 2005—, Nature.

Yin, et al., "Colloidal nanocrystal synthesis and the organic-inorganic interface," Nature, vol. 437, 27 pages, Sep. 29, 2005.

Yu, et al., "Forming Biocompatible and Nonaggregated Nanocrystals in Water Using Amphiphilic Polymers," J. Am. Chem. Soc., vol. 129, No. 10, 9 pages, 2007.

Yang, et al., "Multifunctional Magneto-Polymeric Nanohybrids for Targeted Detection and Synergistic Therapeutic Effects on Breast Cancer," *Angew. Chem. Int. Ed.*, 2007, vol. 46, pp. 8836-8839, plus additional 8 pp. of attached Supporting Information.

\* cited by examiner

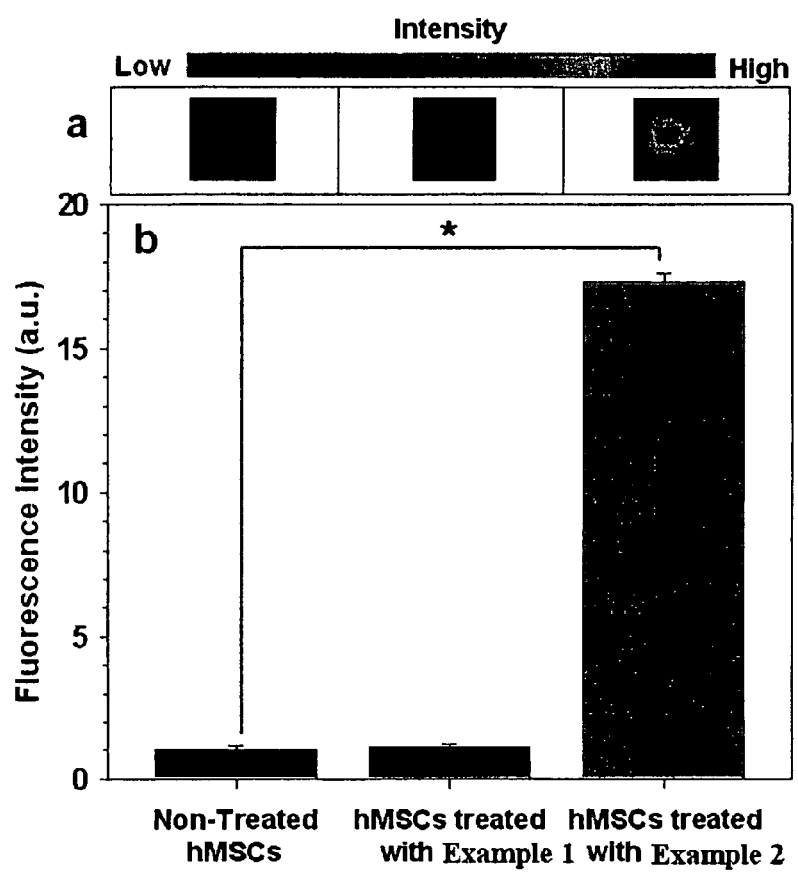

METAL NANOCOMPOSITE, PREPARATION METHOD AND USE THEREOF

BACKGROUND

The technical field relates to nanotechnology, particularly metal nanoparticles. Nanotechnology includes technologies for manipulating and controlling materials on an atomic or molecular scale, and has a variety of applications in fields including, but not limited to, e.g., electronics, materials, communication, mechanics, medicine, agriculture, energy and environment.

SUMMARY

A metal nanocomposite, a preparation method, and various uses of the metal nanocomposite are provided.

One aspect includes one or more metal nanocomposites having a hydrophobic surface, said hydrophobic surface associated with one or more polymers which have one or more cationic and hydrophilic characteristics. In some embodiments, the hydrophobic surface is bound (optionally chemically bound) to the one or more metal nanoparticles. In some embodiments, the one or more polymers at least partially or optionally completely enclose the hydrophobic surface.

In some embodiments, the hydrophobic surface contains an organic surfactant having one or more hydrophobic moieties, e.g., an alkyl trimethylammonium halide; a saturated fatty acid; an unsaturated fatty acid; a trialkylphosphine; a trialkylphosphine oxide; an alkylamine; an alkyl thiol; a sodium alkyl sulfate; a sodium alkylphosphate; oleic acid; lauric acid; dodecylic acid; and dodecyl amine. In some embodiments, the metal nanoparticle comprises a magnetic metal or a magnetic metal alloy, e.g., platinum (Pt), palladium (Pd), silver (Ag), copper (Cu), gold (Au), cobalt (Co), manganese (Mn), iron (Fe), nickel (Ni), gadolinium (Gd), molybdenum (Mo), $MM'_2O_4$, $M_xO_y$, CoCu, CoPt, FePt, CoSm, NiFe, and NiFeCo, wherein M or M' independently represents cobalt (Co), iron (Fe), nickel (Ni), manganese (Mn), zinc (Zn), gadolinium (Gd), or chromium (Cr), x is a real number of $0<x\leq3$, and y is a real number of $0<y\leq5$.

In some embodiments, the one or more cationic and hydrophilic polymers have an average molecular weight of about 1,000 to about 1,000,000 Mw or from about 2,000 to about 30,000 Mw. In some embodiments, the one or more cationic and hydrophilic polymers have one or more amine groups. In particular embodiments, the one or more cationic and hydrophilic polymers are selected from the group consisting of: polyalkyleneimine; polyallylamine; polyvinylamine; dialkylaminoalkyl dextran; polyacrylamide; chitosan; polyornithine; and polylysine, where the alkyl group has carbon number of 1 to 4.

In some embodiments, the one or more cationic and hydrophilic polymers are bound to an active substance selected from the group consisting of: a cell; an antigen; an antibody; a nucleic acid; a polypeptide; an organic fluorescent material; a carbohydrate; a lipid; a tumor marker-specific binding material; and a pharmaceutically active ingredient. For example, the active substance is bound to one or more amine groups of the one or more cationic and hydrophilic polymers. In some embodiments, the nucleic acid comprises DNA or RNA. In some embodiments, the organic fluorescent material comprises RITC (rhodamin A isothiocyanate) or FITC (fluorescein isothiocyanate). In some embodiments, the tumor marker-specific binding material comprises one or more materials selected from the group consisting of: phosphatidylserine; VEGFR; an integrin receptor; a Tie2 receptor; a somatostatin receptor; a vasointestinal peptide receptor; Herceptin; Rituxan; and folic acid. In some embodiments, the pharmaceutically active ingredient comprises one or more agents selected from the group consisting of: an anticancer agent; an antibiotic; a hormone; a hormone antagonist; interleukin; interferon; a growth factor; a tumor necrosis factor, endotoxin; lymphotoxin; eurokinase; streptokinase; a tissue plasminogen activator; a protease inhibitor; alkylphosphocholine; a radioisotope labeled component; a surfactant; a cardiovascular system drug; a gastrointestinal system drug; and a nervous system drug.

One aspect includes one or more methods for preparing a metal nanocomposite including providing an aqueous solution including one or more cationic and hydrophilic polymers, to an organic solution including one or more metal nanoparticles having a hydrophobic surface, to form an emulsion; and removing the organic solution from the emulsion. In some embodiments, the method further comprises binding the cationic and hydrophilic polymer with an active substance selected from the group consisting of: a cell; an antigen; an antibody; a nucleic acid; a polypeptide; an organic fluorescent material; a carbohydrate; a lipid; a tumor marker-specific binding material; and a pharmaceutically active ingredient.

In some embodiments, the method further comprises performing a thermal decomposition reaction of a hydrophobic surface stabilizer and a precursor of the metal nanoparticle in a solvent to form a metal nanoparticles having a hydrophobic surface. For example, the precursor comprises a metal carbonyl compound or a metal acetylacetonate compound. For example, the organic solution comprises one or more solvents selected from the group consisting of: hexane; chloroform; benzene; diethylether; ethyl acetate; and dichloromethane. For example, the aqueous solution comprises one or more solvents selected from the group consisting of: water; PBS; alcohol; and dimethylsulfoxide. In some embodiments, the emulsion is formed under ultrasonication. In some embodiments, the organic solvent is removed by evaporation.

One aspect includes one or more compositions including one or more of the metal nanocomposites described herein, and one or more pharmaceutically acceptable carriers or excipients. The compositions may include, but are not limited to, compositions useful for detection (e.g., contrast agents), diagnosis, and/or treatment (in vitro and/or in vivo).

One aspect includes a method for using a contrast composition to image the cells or tissues of a subject, the method comprising: (a) administering an effective amount of a contrast composition comprising the metal nanocomposite of claim 1 and a pharmaceutically acceptable carrier or excipient to a subject; and (b) detecting a signal emitted by the metal nanocomposite from the subject to obtain images of the cells or tissues of the subject.

Another aspect includes a method for diagnosing a medical condition, the method comprising: (a) administering an effective amount of a diagnosis composition comprising the metal nanocomposite of claim 1 and a pharmaceutically acceptable carrier or excipient to a subject; and (b) detecting a signal emitted by the metal nanocomposite from the subject to obtain images, wherein the images are compared to a reference standard in order to diagnose a medical condition in the subject.

Another aspect includes method for simultaneously diagnosing and treating a medical condition, the method comprising: (a) administering a therapeutically effective amount of a pharmaceutical composition comprising the metal nanocomposite of claim 1 and a pharmaceutically acceptable carrier or excipient to a subject, wherein the pharmaceutical composition is bound to an active substance; and (b) detecting a signal emitted by the metal nanocomposite from the subject to obtain an image, wherein the image is compared to a reference standard in order to diagnose the medical condition in the subject and the active substance treats the medical condition in the subject.

BRIEF DESCRIPTION OF THE DRAWINGS

FIG. 2 is a series of photographs showing the stability of the illustrative metal nanocomposite of Sample No. 1 according to Example 1.

FIG. 6a is a series of optical images showing, from left toward right, hMSCs, hMSCs contacted with the illustrative metal nanocomposite of Sample No. 1 according to Example 1, and hMSCs contacted with the illustrative fluorescent metal nanocomposite according to Example 2. FIG. 6b is a chart showing the fluorescence intensity of the same samples.

DETAILED DESCRIPTION

Figure 1A:
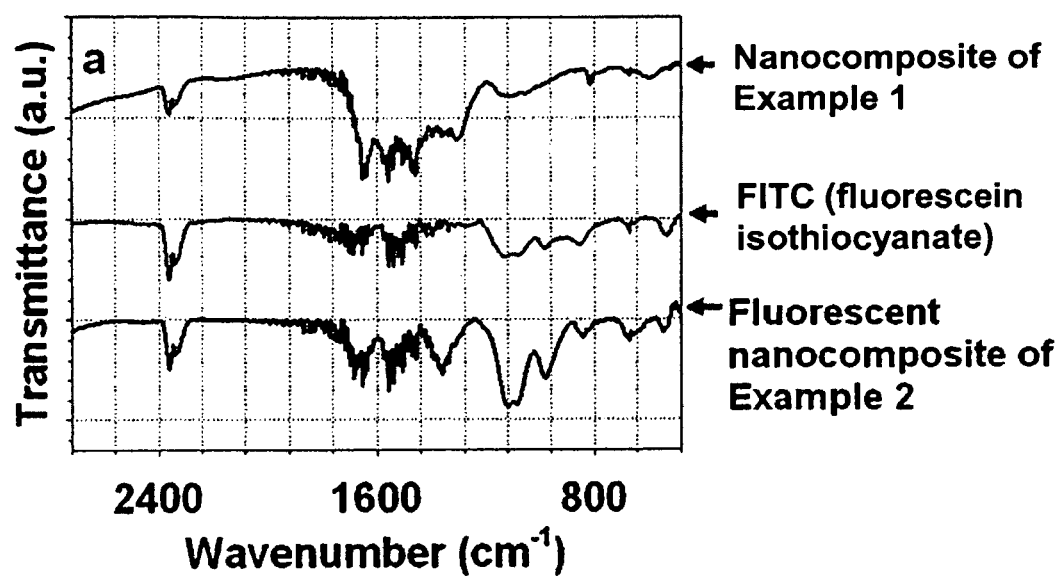
FIGS. 1a and 1b are FT-IR spectra and UV-Vis absorption spectra, respectively, of the illustrative metal composite of Sample No. 1 according to Example 1, the illustrative fluorescent metal nanocomposite of Example 2, and fluorescein isothiocyanate (FITC).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

This disclosure is drawn, inter alia, to metal nanocomposites, as well as related preparation methods, various uses, and methods of using the metal nanocomposites.

Unless explicitly described to the contrary, the word "comprise" and variations such as "comprises" or "comprising", and "having" and/or "including" will be understood to include the information described in the body of the claim, for example, but not to exclude information not explicitly set forth.

As used herein, when referring to a numerical value, the term "about" refers to plus or minus 10% of the enumerated value, unless otherwise stated.

Metal nanoparticles are useful in a broad range of applications, such as but not limited to, separation of biological components, diagnostic probes (e.g., contrast agents), magnetic resonance imaging, biosensors (including giant magnetoresistive sensors), microfluidic sensors, drug/gene delivery, and a magnetic fluid hyperthermia. However, metal nanoparticles that have hydrophobic surfaces may have decreased solubility in water which may impact their use in biological or medical fields in areas such as, but not limited to, drug delivery, biodetection or biolabeling, as well as for catalysis in aqueous solutions.

Accordingly, one aspect is drawn to a metal nanocomposite including one or more metal nanoparticles, the one or more nanoparticles having a hydrophobic surface; and one or more cationic and hydrophilic polymers associated with the hydrophobic surface. In some embodiments, the one or more metal nanoparticles at least partially up to completely form the core of the metal nanocomposite. In some embodiments, the one or more cationic and hydrophilic polymers at least partially up to completely surround or enclose the core of the metal nanocomposite. In some embodiments, the one or more cationic and hydrophilic polymers at least partially up to completely form a shell surrounding or enclosing the core of the metal nanocomposite.

As used herein, the term "at least partially" includes amounts that are detectably greater than not at all, and detectably less than completely. By detectably is meant readings detectable (e.g., using equipment standard in the art) and significant over the error rate (e.g., background) of the instrument and test conditions. In some embodiments, "at least partially" may be expressed as a percentage of completely, or as ranges of percentages of completely. For example, percentages may include, but are not limited to, approximately any integer amount, or approximately 1%, 5%, 10%, 15%, 20%, 25%, 30%, 35%, 40%, 45%, 50%, 55%, 60%, 65%, 70%, 75%, 80%, 85%, 90%, 95%, or 99% of completely. For example, ranges of percentages may include, but are not limited to, approximately 1 to 99%, 10 to 99%, 25 to 99%, 50 to 99%, 75 to 99%, 90 to 99%, 1 to 75%, 1 to 50%, 1 to 25%, 1 to 10%, 10 to 25%, 10 to 50%, 10 to 75%, 10 to 99%, 25 to 50%, 25 to 75%, 25 to 99%, 50 to 75%, 50 to 90%, 50 to 99%, 75 to 90%, or 75 to 99% of completely. As used herein, the term "completely" refers to approximately 100% as measured using standard equipment as described above.

In some embodiments, the hydrophobic surface of the one or more metal nanoparticles is associated with one or more hydrophobic surface stabilizers. In some embodiments, the association between the hydrophobic surface of the one or more metal nanoparticles and the one or more hydrophobic surface stabilizer may be through one or more chemical bonds, optionally one or more of covalent, ionic, hydrogen, and/or van de Waal's bonds. The presence of the one or more hydrophobic surface stabilizers may facilitate the synthesis of the nanocomposite optionally through enhancing (and optionally maintaining) the dispersion of the nanocomposite in, for example, an organic solvent. In some embodiments, the one or more hydrophobic surface stabilizers maintain the one or more metal nanoparticles in a nano-scaled size and homogenously dispersed (e.g., non-aggregated) state in organic solvents. In addition, hydrophobic interactions between one or more of the one or more metal nanoparticles may be enhanced (or formed), thereby at least partially ensuring that the one or more metal nanoparticles are stably maintained in the core of the nanocomposite.

As used herein, the terms "associate", "associated", and "associating" include one or more interactions between one or more constituents of the metal nanocomposite. For example, the association of the one or more cationic and hydrophilic polymers with the hydrophobic surface of the one or more metal nanoparticles, and/or the association between the one or more hydrophobic surface stabilizers and the hydrophobic surface of the one or more metal nanoparticles. Such interactions may include one or more physical and/or chemical interactions including, but not limited to, one or more chemical bonds. Such interactions may include a series of transient interactions (e.g., hydrogen bonds), or may be include a largely permanent interactions (e.g., covalent bond).

In some embodiments, the metal nanocomposite is characterized as stable and dispersed in an aqueous medium. As the hydrophobic surface of the one or more metal nanoparticles is at least partially (or completely) surrounded with one or more cationic and hydrophilic polymers, the hydrophobic surface of the one or more metal nanoparticles is modified such that the surface is at least partially (or completely) hydrophilic. Although not wishing to be bound by any particular mechanism, the electrostatic repulsion between the metal nanocomposites having cationic surface charges is believed to enhance stability and dispersion particularly in aqueous environments. The association of the one or more cationic and hydrophilic polymers with the one or more metal nanoparticles stabilizes the metal nanocomposite for use in vivo in a variety of biological and/or medical applications, for example.

As used herein, the one or more cationic and hydrophilic polymers may form a partial or complete "shell" at least partially or completely surrounding the one or more metal nanoparticles in the core of the metal nanocomposite. The partial or complete "shell" can be a variety of thicknesses. However, in illustrative embodiments, the shell has an approximate average range of thickness of 1 to 40 nm, 1 to 35 nm, 1 to 30 nm, 1 to 25 nm, 1 to 20 nm, 1 to 15 nm, 1 to 10 nm, 1 to 5 nm, 5 to 40 nm, 5 to 35 nm, 5 to 30 nm, 5 to 25 nm, 5 to 20 nm, 5 to 15 nm, 5 to 10 nm, 10 to 40 nm, 10 to 35 nm, 10 to 30 nm, 10 to 25 nm, 10 to 15 nm, 15 to 40 nm, 15 to 35 nm, 15 to 30 nm, 15 to 20 nm, 20 to 40 nm, 20 to 35 nm, 20 to 25 nm, 25 to 40 nm, 25 to 30 nm, 30 to 40 nm, 30 to 35 nm, or 35 to 40 nm. In illustrative embodiments, the shell has an approximate average thickness of 1, 5, 10, 15, 20, 25, 30, 35, or 40 nm.

As used herein, the term "stable," "stability" or "stabilized" reflects the ability of the metal nanocomposite to maintain its integrity and/or characteristic conformation in a variety of environments. In illustrative embodiments, the metal nanocomposite is maintained at a nano-sized scale and in a homogenously dispersed state (e.g., without significant increases in the formation of aggregates) in a variety of environments (e.g., following the initial dispersion) without requiring additional disruption. In illustrative embodiments, the environments include both organic and aqueous environments.

In some embodiments, the aqueous environment may include, but is not limited to, aqueous media of a variety of pH and ionic concentrations. In illustrative embodiments, the pH may include ranges from approximately 4.5 to approximately 11.5. In some embodiments, the metal nanocomposite may be stable in pH of one or more of approximately 4.5, 5.0, 5.5, 6.0, 6.5, 7.0, 7.5, 8.0, 8.5, 9.0, 9.5, 10.0, 10.5, 11.0, or 11.5 pH. In illustrative embodiments, the ionic concentration (e.g., from NaCl) may include ranges from approximately 0.005 M to approximately 1.5 M. In some embodiments, the metal nanocomposite may be stable in ionic concentrations of one or more of approximately 0.005, 0.01, 0.05, 0.1, 0.5, 1.0, or 1.5 M concentrations.

In some embodiments, the cationic polymer may be associated with (optionally through one or more chemical bonds) to one or more active substances. In illustrative embodiments, the one or more active substances may optionally be at least partially anionic. In some embodiments, the one or more active substances may include, but are not limited to, one or more cells or cellular components, such as but not limited to, membranes, nucleic acids (DNA, RNA, genes), polypeptides, carbohydrates, and/or lipids. The metal nanocomposite may be used in various applications in biological or medical fields such as, but not limited to, drug delivery, diagnosis, or biological labeling.

In some embodiments, the metal of the one or more metal nanoparticles may include a magnetic metal or a magnetic metal alloy, thereby facilitating the use of the metal nanocomposite in magnetism-related applications, for example, as a diagnostic probe (e.g., contrast agent) of magnetic resonance imaging (MRI); or in diagnosing and/or treating diseases by delivering the active substance (e.g., biologically or pharmaceutically active ingredient) to a target or target region.

As used herein, the metal or metal alloy is not limited. Any metal and/or metal alloy appropriate to a desired use may be used without limitation. In illustrative embodiments, the magnetic metal or magnetic metal alloy includes, but is not limited to, one or more magnetic metal selected from the group consisting of platinum (Pt), palladium (Pd), silver (Ag), copper (Cu), gold (Au), cobalt (Co), manganese (Mn), iron (Fe), nickel (Ni), gadolinium (Gd), molybdenum (Mo), $MM'_2O_4$, $M_xO_y$, CoCu, CoPt, FePt, CoSm, NiFe, and NiFeCo. In the formula $MM'_2O_4$ and $M_xO_y$, M or M' independently represents cobalt (Co), iron (Fe), nickel (Ni), manganese (Mn), zinc (Zn), gadolinium (Gd), or chromium (Cr), x is a real number of $0<x\leq3$, and y is a real number of $0<y\leq5$.

As used herein, the one or more metal nanoparticles have a variety of diameters limited by, for example, their intended application. For example, use in one or more biological and/or medical applications, where the size of the metal nanocomposite must be appropriate for use in vivo and/or in vitro. In illustrative embodiments, the metal nanoparticle has an average diameter in a range of approximately 1 to 1,000 nm, 1 to 900 nm, 1 to 750 nm, 1 to 500 nm, 1 to 250 nm, 1 to 100 nm, 1 to 75 nm, 1 to 50 nm, 1 to 25 nm, 1 to 10 nm, 10 to 1000 nm, 10 to 900 nm, 10 to 750 nm, 10 to 500 nm, 10 to 250 nm, 10 to 100 nm, 10 to 75 nm, 10 to 50 nm, 10 to 25 nm, 25 to 1000 nm, 25 to 900 nm, 25 to 750 nm, 25 to 500 nm, 25 to 250 nm, 25 to 100 nm, 25 to 75 nm, 25 to 50 nm, 50 to 1000 nm, 10 to 900 nm, 50 to 750 nm, 50 to 500 nm, 50 to 250 nm, 50 to 100 nm, 75 to 1000 nm, 75 to 900 nm, 75 to 750 nm, 75 to 500 nm, 75 to 250 nm, 75 to 100 nm, 100 to 1000 nm, 100 to 900 nm, 100 to 750 nm, 100 to 500 nm, 100 to 250 nm, 250 to 1000 nm, 250 to 900 nm, 250 to 750 nm, 250 to 500 nm, 500 to 1000 nm, 500 to 750 nm, 750 to 1000 nm, or 900 to 1000 nm. In illustrative embodiments, the metal nanoparticle has an average diameter of approximately 1, 5, 10, 25, 50, 100, 250, 500, 750, 900, or 1000 nm.

As used herein, the one or more hydrophobic surface stabilizers associated with the hydrophobic surface of the one or more metal nanoparticles in the metal nanocomposite may include, but are not limited to, one or more surfactants (optionally organic surfactants) having one or more hydrophobic moieties. In illustrative embodiments, the surfactant includes, but is not limited to, a cationic surfactant such as, but not limited to, an alkyl trimethylammonium halide; a neutral surfactant selected from a saturated or unsaturated fatty acid such as, but not limited to, oleic acid, lauric acid, or dodecylic acid, trialkylphosphine or trialkylphosphine oxide such as trioctylphosphine oxide, trioctylphosphine, or tributylphosphine, an alkylamine such as dodecyl amine, oleic amine, trioctylamine, or octylamine, or an alkyl thiol; or an anionic surfactant such as, but not limited to, sodium alkyl sulfate or sodium alkylphosphate.

As used herein, the term, "cationic and hydrophilic polymer" refers to a positively charged polymer with hydrophilic properties. In illustrative embodiments, the polymer is optionally a nitrogen-containing polymer, such as one containing an amino, imino or amido group, one or more of which may include primary, and secondary amino groups. In illustrative embodiments, the one or more amine groups are optionally associated with and/or form a chemical bond with the one or more active substances. Although not intending to be bound by a particular mechanism, the nitrogen of the amine group forms hydrogen bonds with the hydrogen of water molecules, optionally increasing the stability of the metal nanocomposite in aqueous medium such as those used in the biological or pharmaceutical applications such as drug delivery in vivo.

In illustrative embodiments, one or more nitrogen-containing polymers include, but are not limited to, polyalkyleneimine, polyallylamine, polyvinylamine, dialkylaminoalkyl dextran, polyacrylamide, chitosan, polyornithine, and polylysine, where the alkyl group has carbon number of 1 to 4, as well as those polymers produced by introducing a substituent thereinto. Suitable polyethyleneimine derivatives may be produced by alkylation, arboxylation, phenylation, phosphorylation, or sulfonation of a polyethyleneimine up to a desired degree.

In illustrative embodiments, the one or more cationic and hydrophilic polymers have an average molecular weight ranging from approximately 1,000 to 1,000,000, 1,000 to 500,000, 1,000 to 100,000, 1,000 to 50,000, 1,000 to 10,000, 1,000 to 5,000, 1,000 to 2,000, 2,000 to 1,000,000, 2,000 to 500,000, 2,000 to 100,000, 2,000 to 50,000, 2,000 to 10,000, 2,000 to 5,000, 5,000 to 1,000,000, 5,000 to 500,000, 5,000 to 100,000, 5,000 to 50,000, 5,000 to 10,000, 10,000 to 1,000,000, 10,000 to 500,000, 10,000 to 100,000, 10,000 to 50,000, 50,000 to 1,000,000, 50,000 to 500,000, 50,000 to 100,000, 100,000 to 1,000,000, 100,000 to 500,000, and 500,000 to 1,000,000 MW. In illustrative embodiments, the one or more cationic and hydrophilic polymers have an average molecular weight of approximately 1,000, 5,000, 10,000, 15,000, 20,000, 25,000, 30,000, 35,000, 40,000, 75,000, 90,000, 125,000, 150,000, 175,000, 225,000, 250,000, 400,000, 600,000, 750,000, 900,000, or 1,000,000 MW.

As used herein, the term "active substance" refers to one or more substances having biological or pharmaceutical activity. In some embodiments, the one or more active substances are capable of binding the cationic and hydrophilic polymer, optionally through at least one anionic moiety. In illustrative embodiments, various biologically or pharmaceutically active substances are associated with the surface of the metal nanocomposite, optionally through a chemical bond to the cationic group, e.g., an amine group of the cationic and hydrophilic polymer. In illustrative embodiments, the metal nanocomposite is used to deliver various active substances into one or more in vivo target regions. In illustrative embodiments, the metal nanocomposite is used to provide one or more active substances useful in various biological or pharmaceutical applications to one or more targets or target regions in vivo, e.g., such as a contrast agent for magnetic resonance imaging, a drug delivery in vivo, and/or for diagnosis or bio-labeling in an organism.

In illustrative embodiments, the biologically active substance includes, but is not limited to, a cell, an antigen, an antibody, a polypeptide, a nucleic acid, a carbohydrate, a lipid, an organic fluorescent material, and a tumor marker-specific binding material. The nucleic acid includes, but is not limited to, a synthetic or isolated natural, linear or circular, double-stranded or single-stranded, DNA and/or RNA fragment designating a precise succession of nucleotides, modified or otherwise. The cell includes, but is not limited to, a stem cell such as hMSCs (bone marrow-derived human mesenchymal stem cells). The polypeptide includes, but is not limited to, protein A or protein G. The organic fluorescent material includes, but is not limited to, RITC (rhodamine A isothiocyanate) or FITC (fluorescein isothiocyanate).

The tumor marker-specific binding material includes, but is not limited to, any biologically active substance that is specifically bound to "tumor markers" such as a ligand, an antigen, or a receptor that tumor cells specifically express or secrete unlike normal cells. When the tumor marker is a ligand, the active substance includes, but is not limited to, phosphatidylserine being specifically bound to C2 of synaptotagmin I or annexin V, VEGFR being specifically bound to VEGF, an integrin receptor being specifically bound to integrin, a Tie2 receptor being specifically bound to angiopoietin 1, 2, a somatostatin receptor being specifically bound to somatostatin, or a vasointestinal peptide receptor being specifically bound to vasointestinal peptide. When the tumor marker is an antigen, the active substance includes, but is not limited to, Herceptin being specifically bound to a carcinoembryonic antigen (large intestine cancer-labeling antigen) or a HER2/neu antigen (breast cancer-labeling antigen), or Rituxan being specifically bound to a prostate-specific membrane antigen (prostate cancer-labeling antigen). When the tumor marker is a receptor such as but not limited to a folic acid receptor, the active substance includes being specifically bound to the receptor.

As used herein, the term "pharmaceutically active substance" refers to any material having a desired therapeutic, prophylactic or diagnostic activity including, but not limited to, proteins, peptides and chemicals. The pharmaceutically active substance may include recombinantly or synthetically prepared substances and/or other substances isolated from natural sources.

The pharmaceutically active substance includes, but is not limited to, an anticancer agent such as paclitaxel or cisplatin, antibiotic, hormone, hormone antagonist, interleukin, interferon, a growth factor, a tumor necrosis factor, an endotoxin, a lymphotoxin, a eurokinase, a streptokinase, a tissue plasminogen activator, a protease inhibitor, an alkylphosphocholine, a radioisotope labeled component, a surfactant, a cardiovascular system drug, a gastrointestinal system drug, or a nervous system drug.

One aspect includes a composition for use as one or more of a therapeutic, a prophylactic, delivering, diagnostic or labeling use. In some embodiments, the metal nanocomposite is administered to a subject. As used herein, the "administration" of an agent or drug to a subject or subject includes any route of introducing or delivering to a subject a compound to perform its intended function. Administration can be carried out by any suitable route, including orally, intranasally, parenterally (intravenously, intramuscularly, intraperitoneally, or subcutaneously), subcutaneously, intramuscularly, intradermally, intrathecally, intraoccularly, rectally, iontophoretically, or topically. Administration includes self-administration and the administration by another.

As used herein, the term "subject" means the subject is a mammal, such as a human, but can also be an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like).

In some embodiments, an effective amount of the metal nanocomposites is used as a therapeutic, a prophylactic, delivering, diagnostic or labeling use. As used herein, the term "effective amount" or "pharmaceutically effective amount" or "therapeutically effective amount" of a composition, is a quantity sufficient to achieve a desired imaging and/or therapeutic and/or prophylactic effect, e.g., an amount which results in the prevention of, or a decrease in, the symptoms associated with a disease/medical condition that is being treated, or the quantity sufficient to achieve a desired diagnostic or imaging outcome. The amount of a composition administered to the subject will depend on the type and severity of the disease or on the characteristics of the individual, such as general health, age, sex, body weight and tolerance to drugs. The skilled artisan will be able to determine appropriate dosages depending on these and other factors. The compositions can also be administered in combination with one or more additional therapeutic compounds.

The magnetic metal nanocomposite can be used for diagnosing and/or treating medical conditions or diseases, delivering the active substance such as tumor marker-specific binding material, a diagnosis composition for medical conditions or diseases, and a labeling composition for diagnosis (magnetic resonance imaging, giant magnetoresistive sensors, and micro fluidic sensors). As used herein, the term "medical condition" includes, but is not limited to, any condition or disease manifested as one or more physical and/or psychological symptoms for which treatment and/or prevention is desirable, and includes previously and newly identified diseases and other disorders. For example, a medical condition may include, but is not limited to, cancer, a hyperproliferative disorder, bacterial infection, fungal infection, or viral infection.

Typically, an effective amount of a contrast composition or a diagnosis composition comprising the metal nanocomposite and a pharmaceutically acceptable carrier or excipient is administered to a subject. The signal emitted by the metal nanocomposite from the subject is detected to obtain images of the cells or tissues of the subject. In some embodiments, the images are compared to a reference standard in order to diagnose a medical condition in the subject. As used herein, the term "reference standard" is the pattern of images produced in either a reference standard population or a single subject prior to administration of a compound. For example, a reference standard can be obtained from subjects for diagnosis or research or can be obtained from undiseased individuals, as controls or for basic research.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a disorder if, after receiving a therapeutic amount of the metal nanocomposite materials, the subject shows observable and/or measurable reduction in or absence of one or more signs and symptoms of a particular disease or condition. For example, for cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. It is also to be appreciated that the various modes of treatment or prevention of medical conditions as described are intended to mean "substantial", which includes total but also less than total treatment or prevention, and wherein some biologically or medically relevant result is achieved.

One aspect includes one or more methods for preparing a metal nanocomposite including providing an aqueous solution containing one or more cationic and hydrophilic polymers to an organic solution containing one or more metal nanoparticles having hydrophobic surface, to form an emulsion; and removing the organic solvent from the emulsion. The method optionally further includes associating (optionally forming a chemical bond) the cationic and hydrophilic polymer with an active substance as described above.

In accordance with the above method, an organic solution including one or more metal nanoparticles with hydrophobic surfaces may be prepared by known methods.

The nanoparticle can be prepared by a) reacting the hydrophobic surface stabilizer with a precursor of the metal nanoparticle in a solvent; b) thermally decomposing the resultant of a) to form the metal nanoparticle bound or optionally chemically bound to the hydrophobic stabilizer; and c) dissolving the metal nanoparticle in the organic solvent. Thus, the metal nanoparticle in which the surface is coordinately bound to a stabilizer can be stably synthesized in an organic solvent. Particularly, the metal nanoparticles can maintain the nano-scaled size distribution and homogeneous dispersion in the organic solvent.

Precursors of the metal nanoparticle include metal compounds having ligands such as —CO, —NO, —$C_5H_5$, alkoxide, and so on, which is bound to the magnetic metal or metal alloy as described above. Examples of the precursors include metal carbonyl compounds such as iron pentacarbonyl, ferrocene, or manganese carbonyl, metal acetylacetonate compounds such as iron acetylacetonate or manganese acetylacetonate, and so on.

The organic solvent for reacting the precursor and the hydrophobic surface stabilizer may include a solvent having a high boiling point near to the thermal decomposition temperature at which the reactant of the precursor and the hydrophobic surface stabilizer is heated and thus thermally decomposed to form the metal nanoparticle, for example 50 to 500° C. The examples of organic solvent may include, but are not limited to, an ether solvent, a heterocyclic solvent, an aromatic solvent, a sulfoxide solvent, an amide solvent, an alcoholic solvent, a hydrocarbon solvent, and water. Examples of the solvent include, but are not limited to, octyl ether, butyl ether, hexyl ether, decyl ether, benzyl ether, pyridine, THF (tetrahydrofuran), toluene, xylene, mesitylen, benzene, DMSO (dimethylsulfoxide), DMF (dimethylformamide), octanol (octyl alcohol), decanol, pentane, hexane, heptane, octane, decane, dodecane, tetradecane, hexadecane, and water.

After reacting the precursor and the hydrophobic surface stabilizer, the resultant was thermally decomposed to grow up the metal nanoparticles and to provide metal nanoparticles with specific size and shape. The heating temperature during the thermal decomposition can be adjusted depending upon the kinds of the precursor and the hydrophobic surface stabilizer, for example, it may be heated the resultant up to the temperature ranging from approximately 50 to 500° C., 100 to 450° C., or 250 to 400° C. The thermal decomposition may be performed by preparing metal nanoparticles bound to the hydrophobic surface stabilizer; and separating and purifying the same in accordance with the conventional method.

The organic solution is prepared by dissolving the metal nanoparticles in an organic solvent. Any organic solvent being capable of dissolving the metal nanoparticle having a hydrophobic surface can be used. The organic solvent includes, but is not limited to, hexane, chloroform, benzene, diethylether, ethylacetate or dichloromethane.

The aqueous solution may be prepared by dissolving the cationic and hydrophilic polymer in an aqueous solvent. The aqueous solvent may be any aqueous solvent being capable of dissolving the cationic and hydrophilic polymer. Examples of the aqueous solvent include, but are not limited to, water, PBS, alcohol and dimethylsulfoxide.

The organic solution including the metal nanoparticle and the aqueous solution including the cationic and hydrophilic polymer are mixed to provide an emulsion. For example, the mixture may be emulsified under ultrasonication. While forming the emulsion, one or more of the metal nanoparticles are coagulated (e.g., aggregated) to form cores of metal nanoparticles due to the intermolecularly hydrophobic interaction. Then, the core is at least partially surrounded with the cationic and hydrophilic polymers.

Subsequently, the organic solvent is removed from the emulsion by a method such as a solvent evaporation, and then, the surface is modified into being hydrophilic to provide a metal nanocomposite useful for various biological or pharmaceutical applications in vivo.

When the metal nanocomposite is magnetic, at least one functional group on the surface can be bound to organic fluorescent material, and thus can be used as a contrast agent for the magnetic resonance imaging.

Furthermore, the metal nanocomposite may be used for a composition for diagnosing diseases such as tumors by delivering active substances being specifically bound to a tumor marker into a target, and then detecting the tumor marker bound to the active substances by magnetic resonance imaging or optical imaging. Alternatively, the metal nanocomposite may be used for a diagnosis and/or treatment pharmaceutical composition by delivering predetermined pharmaceutical active ingredients into organisms.

Such a metal nanocomposite can be made for a contrast agent, a diagnosis composition, or a pharmaceutical composition referring to WO 2007/097593 A1, the entire disclosures of which are hereby incorporated by reference in their entirety into the present specification.

The contrast composition, diagnosis composition, and pharmaceutical composition both for diagnosis and treatment includes any one or more of the above metal nanocomposite and a pharmaceutically acceptable carrier.

The carrier applicable to these compositions includes a carrier and a vehicle used generally in medical field. Specific examples of the carrier include alumina, aluminum stearate, lecithin, a serum protein (e.g., human serum albumin), buffer materials (e.g., various phosphate, glycine, sorbic acid, potassium sorbate, a partial mixture of a saturated vegetable fatty acid and glyceride), water, salts, or electrolytes (e.g., protamine sulfate, disodium hydrogen phosphate, potassium hydrogen phosphate, sodium chloride, and zinc salts), colloidal sillica, magnesium trisilicate, polyvinylpyrrolidone, a cellulose-based substrate, polyethylene glycol, sodium carboxylmethyl cellulose, polyan arylate, wax, polyethylene glycol, or lanolin, but are not limited thereto. Further, these compositions may further include pharmaceutically acceptable lubricant, wetting agent, emulsifier, suspension, or preservative other than these components.

In one embodiment, the composition may be a water-soluble solution for parenteral administration. The water-soluble solution includes a buffer solution such as Hank's solution, Ringer's solution, or physically buffered saline. Water-soluble injection suspension may include viscosity-increasing substances such as sodium carboxyl methylcellulose, sorbitol, or dextran.

The compositions according to other embodiments may be formed as a sterilized formulation for injection of an aqueous or oily suspension. Such suspension may be formulated according to the conventional technology by using the suitable dispersing agent or a wetting agent (for example, Twin 80), and an emulsifier. The sterilized formulation for injection may include a nontoxic and parentally acceptable diluent or a sterilized injection solution or suspension (for example, 1,3-butanediol solution). Useable vehicle and solvent includes mannitol, water, Ringer's solution, and isotonic sodium chloride solution. A sterilized non-volatile oil is generally used as a solvent or an emulsifying medium. For this objects, it may include any less irritating non-volatile oil such as synthetic mono- or di-glyceride.

The above compositions can be used for a contrast composition for magnetic resonance imaging, diagnosing specific diseases/medical conditions, or diagnosing and/or treating specific diseases/medical conditions by delivering pharmaceutical active ingredients into an organism. Such compositions can be applicable by the method including administering the compositions to an organism or a specimen, and sensing signals emitted by the metal nanocomposite from the organism or specimen to obtain images.

As mentioned in the following Examples, it is discovered that the metal nanocomposite can be imaged in the subject. Accordingly, the metal nanocomposite can be used to trace a bound biologically or pharmaceutically active substances such as a cell, organic fluorescent materials, or pharmaceutically active ingredients. Accordingly, through the imaging and analysis, it can be used as a contrast agent for magnetic resonance imaging; or a diagnosis composition or a pharmaceutical composition for diagnosing and/or treating a certain disease.

Compositions according to the embodiments or other embodiments may be administered into the subject through the conventional medicinal way. According to one embodiment, it may be parenterally administered, for example, in intravenous, intraperitoneal, intramuscular, or hypodermic dosage forms.

In addition, in a method of using the contrast composition or a method for diagnosing and/or treating a disease/medical condition, the signal emitted from the metal nanocomposite can be detected by instrumentation using a magnetic field. According to one embodiment, it is detected by magnetic resonance imaging (MRI) device. Particularly, according to another embodiment, the magnetic resonance imaging device is T2 spin-spin relaxation magnetic resonance imaging device.

EXAMPLES

The compositions and methods described herein are further illustrated by the following examples, which should not be construed as limiting in any way.

Example 1

Preparation of a Metal Nanocomposite

Preparation of a metal nanoparticle bound to a hydrophobic surface stabilizer. Metal nanoparticles were prepared using the following thermal decomposition method. Two (2) mmol of iron (III) acetylacetonate, 1 mmol of manganese (II) acetylacetonate, 10 mmol of 1,2-hexadecanediol, 6 mmol of dodecanoic acid, 6 mmol of dodecyl amine, and 60 ml of benzyl ether were mixed under a nitrogen atmosphere. The mixture was pre-heated at 150° C. for 30 min and then, refluxed at 300° C. for 30 min. After cooling to room temperature, the resulting product was purified with an excessive amount of pure ethanol. Metal nanoparticles having approximately 10 nm diameter were obtained.

Preparation of metal nanocomposite enclosed by polyethyleneimine. Hydrophilic metal nanocomposites were prepared using the following nano-emulsion method. Twenty (20) mg of metal nanoparticles (e.g., the metal nanoparticles prepared using the method of Example 1) are dissolved in 4 mL of hexane. Then, 20 mL of a PBS aqueous solution containing 50 mg of polyethyleneimine with an average molecular weight of 25,000 were added thereto and mixed together. After mutual saturation of the organic and the continuous phases, the mixture was emulsified for 10 min under ultrasonification (ULH700S, Ulssohitech) at 420 W. After solvent evaporation, metal nanocomposites enclosed by polyethyleneimine were purified by triple centrifugation at 15,000 rpm and stored under vacuum conditions.

Furthermore, each metal nanocomposite was prepared by varying the weight average molecular weight of polyethyleneimine and the amounts of used metal nanoparticle and polyethyleneimine as shown in Table 1.

TABLE 1

Metal Nanocomposites

| No. of Sample | Amount of used MNPs (mg) | PEI Mw | Amount of PEI (mg) |
|---|---|---|---|
| 1 | 20 | 25,000 | 50 |
| 2 | 10 | 25,000 | 50 |
| 3 | 5 | 25,000 | 50 |
| 4 | 20 | 25,000 | 100 |
| 5 | 10 | 25,000 | 100 |
| 6 | 5 | 25,000 | 100 |
| 7 | 20 | 25,000 | 200 |
| 8 | 10 | 25,000 | 200 |
| 9 | 5 | 25,000 | 200 |
| 10 | 20 | 800 | 50 |
| 11 | 10 | 800 | 50 |
| 12 | 5 | 800 | 50 |
| 13 | 20 | 800 | 100 |
| 14 | 10 | 800 | 100 |
| 15 | 5 | 800 | 100 |
| 16 | 20 | 800 | 200 |
| 17 | 10 | 800 | 200 |
| 18 | 5 | 800 | 200 |

Figure 1B:
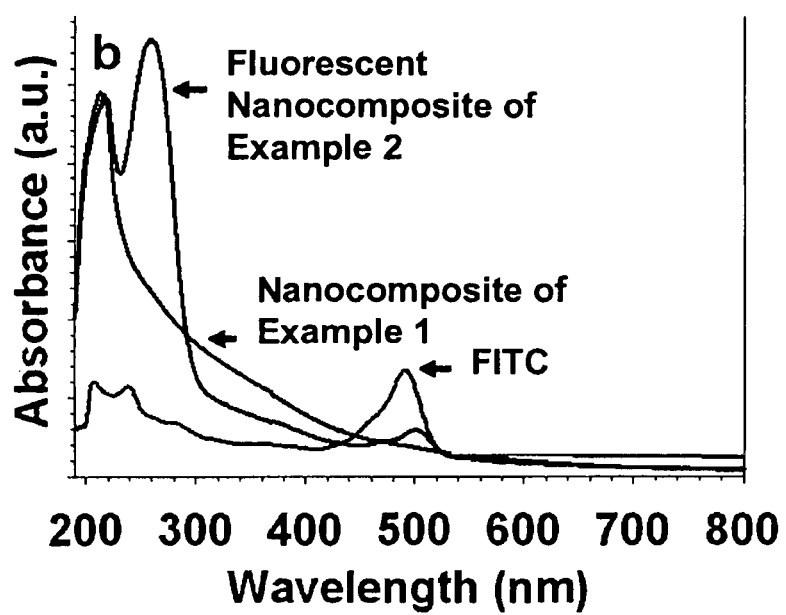

Chemical structures of the metal nanoparticles and the metal nanocomposites of Sample No. 1 were analyzed by using FT-IR spectrum and UV-Vis absorption spectrum. FT-IR spectra and UV-Vis absorption spectra are shown in FIGS. 1A and 1B. In FIG. 1A, a brown line denotes the metal nanoparticle and a green line denotes the metal nanocomposite of Sample no. 1.

Example 2

Preparation of Fluorescent Metal Nanocomposites

Metal nanocomposites bound to organic fluorescent materials were prepared by conjugating FITC (0.58 mg/mL) with polyethyleneimine (3.64 mg/mL) with an average molecular weight of 25,000 on the surface of metal nanocomposites (13 mg/mL) (e.g., the metal nanoparticles prepared using the method of Example 1) for 12 hours in a darkroom. Isothiocyanate groups of the FITC showed high reactivity for amine groups of the polyethyleneimine. The resulting products were purified by triple centrifugation at 6,800 rpm using a centrifugal filter (MWCO 1,000, Amicon Ultra-15, Millipore).

Chemical structures of the fluorescent nanocomposites were analyzed by using FT-IR spectrum and UV-Vis absorption spectrum, and the results were shown in FIGS. 1a and 1b.

Referring to FIG. 1a, the metal nanocomposite of Sample No. 1 according to Example 1 shows a spectrum peak of polyethyleneimine at around 1,600 cm$^{-1}$ due to a primary amine group. It also shows another peak of Fe-O bond at around 585 cm$^{-1}$. The fluorescent metal nanocomposite according to Example 2 shows a peak due to the isothiocyanate (—N=C=S) group of FITC at around 2,125 cm$^{-1}$. In addition, it still shows a peak of polyethyleneimine, indicating that it is not altered but maintained during the preparation process of the metal nanocomposite bound to the organic fluorescent material. Another peak of a new isothiocanate (—N=C=S—H—) group of the fluorescent metal nanocomposite of Example 2 was shown at around 1,350 cm$^{-1}$.

To further confirm the presence of FITC in the fluorescent metal nanocomposite of Example 2, UV-vis absorption spectroscopy was performed (see FIG. 1b). The UV-vis absorption spectrum had characteristic bands at 245 nm and 492 nm respectively due to a metal nanoparticle and FITC as an organic fluorescent material in the metal nanocomposite. These results show the preparation of the polyethyleneimine enclosed metal nanoparticles. These results also indicate that FITC was also bound to the surface of the metal nanocomposite.

Example 3

Stability Evaluation of a Metal Nanocomposite

Figure 2A:
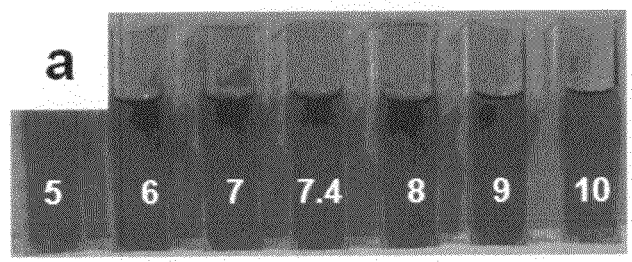
FIG. 2a is a photograph of the stability of the illustrative metal nanocomposite in aqueous medium with a broad pH range.

To evaluate stability in aqueous mediums with broadly-ranged pH, stability of the metal nanocomposite of Sample No. 1 according to Example 1 was evaluated in aqueous solutions with pH 5, 6, 7, 7.4, 8, 9, or 10 for one month. The result is shown in FIG. 2a and indicates that the metal nanocomposite is stable over a broad range of pH.

Figure 2B:
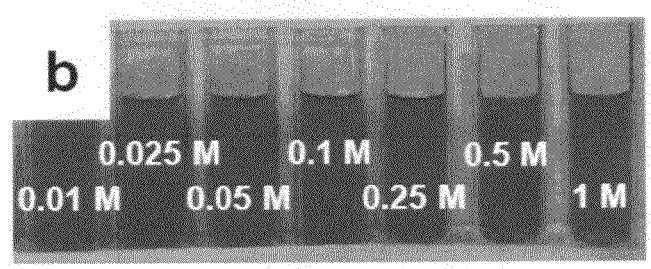
FIG. 2b is a photograph of the stability of the illustrative metal nanocomposite in aqueous medium with a broad range of NaCl concentration.

To evaluate stability in aqueous mediums with broadly-ranged NaCl concentration, stability of the metal nanocomposite of Sample No. 1 according to Example 1 was evaluated in aqueous solutions with NaCl concentrations of 0.01M, 0.025M, 0.05M, 0.1M, 0.25M, 0.5M, or 1M for one month. The result is shown in FIG. 2b and indicates that the metal nanocomposite is stable over a broad range of NaCl concentrations.

Figure 2C:
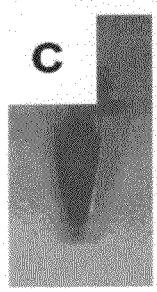
FIG. 2c is a photograph of the stability of the illustrative metal nanocomposite in serum.

To evaluate stability in serum, stability of the metal nanocomposite of Sample No. 1 according to Example 1 was evaluated in a serum for one month. The result is shown in FIG. 2c and indicates the metal nanocomposite is stable in serum.

In summary, the metal nanocomposite of Sample No. 1 according to Example 1 was found out to have dispersion, particle uniformity, and stability for over one month in the environments similar to an in vivo environment, as well as the aqueous mediums with broadly-ranged pH and NaCl concentrations.

To evaluate colloidal stability in PBS, the metal nanocomposites of Sample Nos. 1 to 18 according to Example 1 were evaluated regarding colloidal stability in PBS (10 Mm, pH 7.4). The metal nanocomposites of Sample Nos. 1 to 9 showed colloidal stability but the metal nanocomposites of Sample Nos. 10 to 18 were not stable. When the metal nanocomposites were prepared using polyethyleneimine with a weight average molecular weight of 25,000. The metal nanocomposites had colloidal stability and dispersed in aqueous medium. However, when the metal nanocomposites were prepared using polyethyleneimine with a weight average molecular weight of 800, the metal nanocomposites had deteriorated stability and dispersion in aqueous medium.

Example 4

Cytotoxicity Evaluation of Metal Nanocomposite

Figure 3:
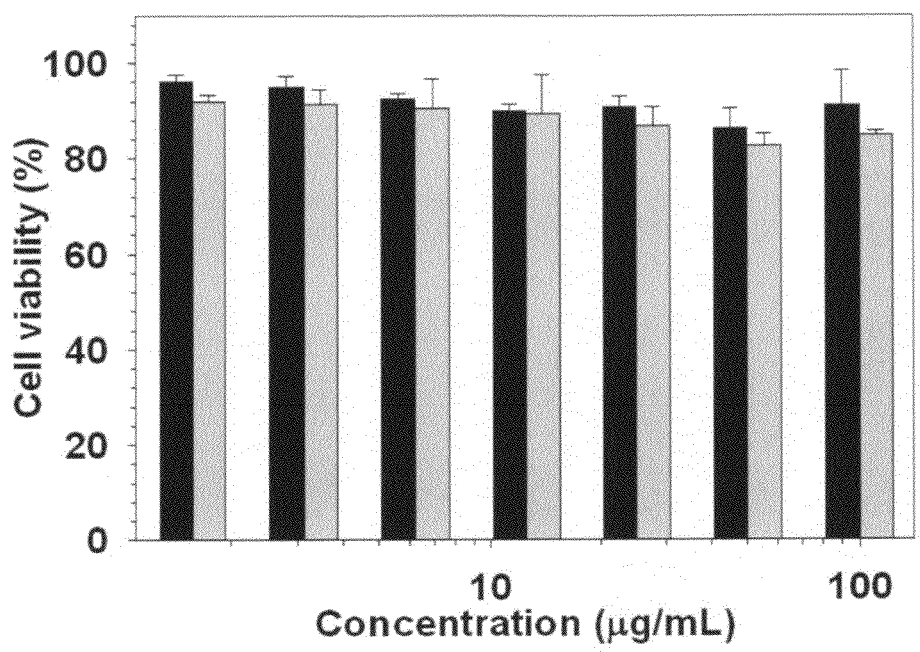
FIG. 3 is a chart showing the in vitro cytotoxicity of the illustrative metal nanocomposite of Sample No. 1 according to Example 1 (black bar) and the illustrative fluorescent metal nanocomposite according to Example 2 (open bar).

In vitro cytotoxicity of the metal nanocomposite of Sample No. 1 according to Example 1 and the fluorescent metal nanocomposite according to Example 2 were evaluated using a MTT (3-(4,5-dimethylthiazol-2-yl)-2,5-diphenyl tetrazolium bromide) analysis method. The results are shown in FIG. 3. Referring to FIG. 3, the cell survival rate was over 80% in a concentration ranging from 0.8 to 100 μg/mL MTT. This result indicates that the metal nanocomposite of Sample No. 1 according to Example 1 and the fluorescent metal nanocomposite according to Example 2 appear biocompatible for a contrast agent, diagnosis composition, pharmaceutical composition, or and the like, are expected to show similar results. Accordingly, the metal nanocomposites are useful for in vivo diagnostic and pharmaceutical compositions.

Example 5

Labeling Efficiency Evaluation of hMSCs

Labeling efficiency as a tracking marker for hMSCs were evaluated for the metal nanocomposite of Sample No. 1 according to Example 1 and the fluorescent metal nanocomposite according to Example 2. The microscopic images of hMSCs treated with the fluorescent metal nanocomposite (FIG. 4c and FIG. 4f) and hMSCs treated with the metal nanocomposite of Sample No. 1 (FIG. 4b and FIG. 4e) were compared to that of hMSCs with no treatment (FIG. 4a and FIG. 4d).

Figure 4:
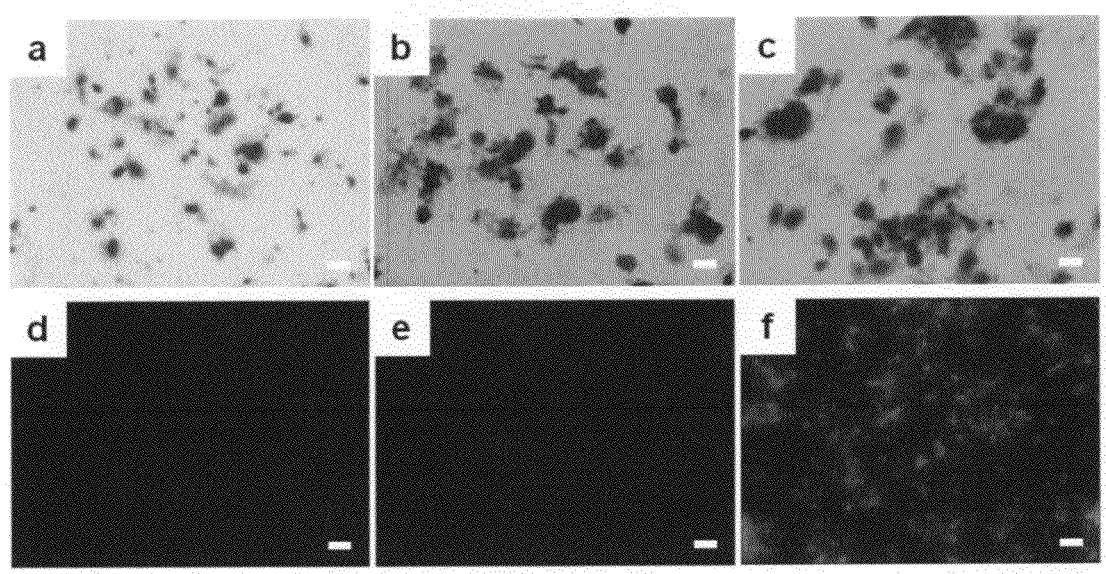
FIG. 4a to FIG. 4f are microscopic images of hMSCs contacted with the illustrative fluorescent metal nanocomposite (FIG. 4c and FIG. 4f) and hMSCs contacted with the illustrative metal nanocomposite of Sample No. 1 (FIG. 4b and FIG. 4e) as compared with that of hMSCs not contacted with the metal nanocomposites (FIG. 4a and FIG. 4d).

The microscopic images of Prussian blue stained hMSCs were provided in panels a to c of FIG. 4 in order to compare with the microscopic images. Referring to panels a to c of FIG. 4, the microscopic images of hMSCs treated with the metal nanocomposite of Sample No. 1 or the fluorescent metal nanocomposite of Example 2 show that the metal nanocomposites were clearly taken up by the hMSCs. Accordingly, hMSCs treated with the metal nanocomposite of Sample No. 1 or the fluorescent metal nanocomposite of Example 2 were confirmed to have a high degree of labeling and potential utility as a hMSC tracking marker via magnetic resonance imaging.

The fluorescent microscope images of DAPI stained hMSCs are shown in panels d to f of FIG. 4. Referring to panel d to f of FIG. 4, hMSCs treated with the fluorescent metal nanocomposite according to Example 2 interacted with FITC and thereby, produced strong fluorescence (FIG. 4f), while hMSCs with no treatment (FIG. 4d) or treated with the metal nanocomposite according to Example 1 did not produce any fluorescence. From the results, hMSCs treated with the fluorescent metal nanocomposite according to Example 2 were confirmed to a high degree of labeling and potential utility as an hMSC tracking marker via optical imaging by using a fluorescent microscope and the like.

Example 6

MR and Optical Contrast Efficiency of FPMNs for Stem Cells (hMSCs) Treated with a Metal Nanocomposite The metal nanocomposite of Sample No. 1 according to Example 1 and the fluorescent metal nanocomposite according to Example 2 were evaluated for contrast efficiency in magnetic resonance imaging and optical imaging methods.

Figure 5:
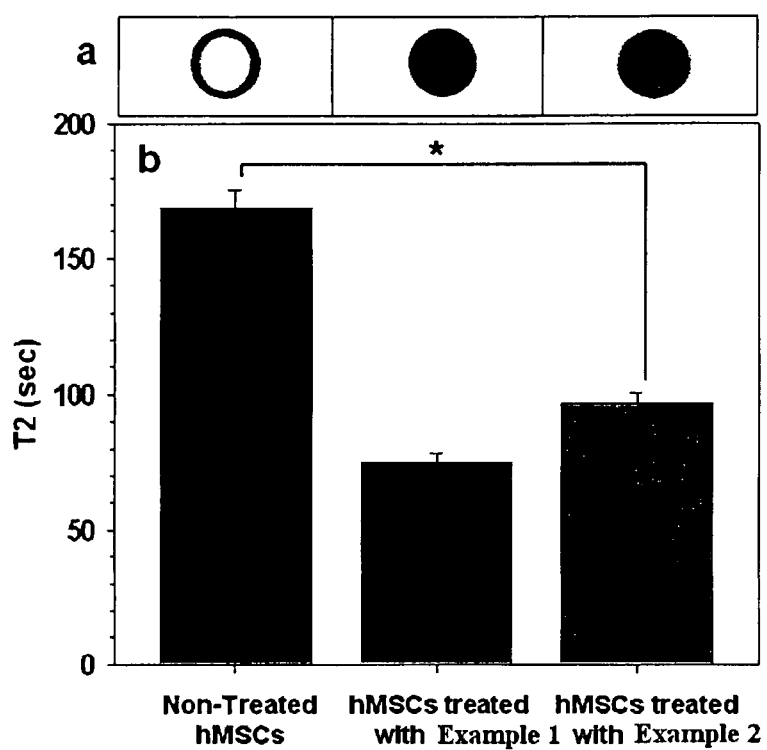
FIG. 5a is a series of magnetic resonance images showing, from left toward right, bone marrow-derived human mesenchymal stem cells (hMSCs), hMSCs contacted with the illustrative metal nanocomposite according to Example 1, and hMSCs contacted with the illustrative fluorescent metal nanocomposite according to Example 2.
FIG. 5b is a chart showing the T2 values of the same samples.
Figure 2C:
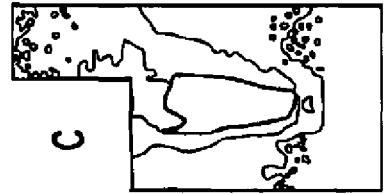
Figure 2A:
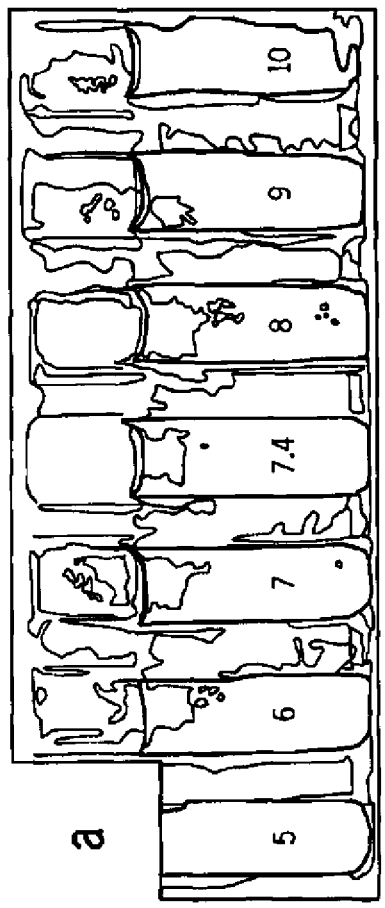
Figure 2B:
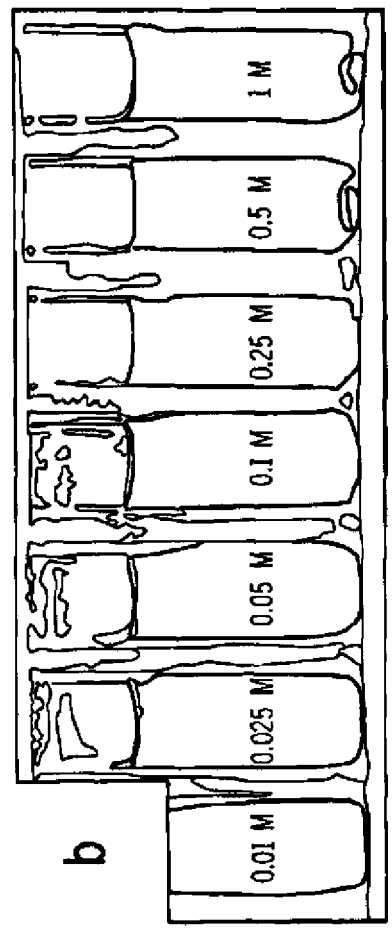

T2-weighted magnetic resonance images of hMSCs treated with the metal nanocomposite and the fluorescent metal nanocomposite were compared with untreated hMSCs. Referring to FIG. 5a, the magnetic resonance images of hMSCs treated with the metal nanocomposite and the fluorescent metal nanocomposite had blacker color than those of hMSCs with no treatment. Therefore, the metal nanocomposite or fluorescent metal nanocomposite was found out to have efficient cellular uptake efficiency. Although not intending to be bound by a particular mechanism, the cationic surface of the fluorescent metal nanocomposite or the metal nanocomposite may increase the affinity of the metal nanocomposite for the anionic cell membrane of hMSCs due to the ionic attraction to each other. In addition, the relative T2 value (57.2±4.0%) of hMSCs treated with the fluorescent metal nanocomposite showed sufficient cellular uptake efficiency (refer to T2 graph in FIG. 5b).

These results indicate that the metal nanocomposite according to Example 1 and the fluorescent metal nanocomposite according to Example 2 can be used as an effective contrast composition or a diagnostic composition, since the metal nanocomposites not only have cellular uptake efficiency, but also can emit a signal for magnetic resonance imaging. Accordingly, the metal nanocomposite materials described herein are useful as contrast agents for imaging cells.

FIG. 6 shows the optical image and fluorescent intensity of hMSCs treated with the metal nanocomposite of sample No. 1 according to Example 1 and the fluorescent metal nanocomposite according to Example 2 compared to hMSCs with no treatment. Referring to FIG. 6a and FIG. 6b, the hMSCs treated with the fluorescent metal nanocomposite had increased optical image strength and fluorescent intensity comparing with those with no treatment or treated with the metal nanocomposite. Accordingly, the fluorescent metal nanocomposite was confirmed to be useful as an hMSCs tracking marker via optical imaging.

The evaluation results of Examples 5 and 6 show that the metal nanocomposite of Example 1 and the fluorescent metal nanocomposite of Example 2 have high binding efficiency with a cell, and can produce a signal. As such, the metal nanocomposites are useful in methods for MRI or optical imaging of cells or tissues.

Equivalents

The present disclosure is not to be limited in terms of the particular embodiments described in this application, which are intended as single illustrations of individual aspects of. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B.".

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A metal nanocomposite comprising one or more metal nanoparticles having a hydrophobic surface; and one or more cationic and hydrophilic polymers associated with the hydrophobic surface;
   wherein:
   the one or more metal nanoparticles is $MnFe_2O_4$;
   the hydrophobic surface contains an organic surfactant having one or more hydrophobic moieties; and
   the one or more cationic and hydrophilic polymers are selected from the group consisting of: polyethyleneimine, polyacrylamide, and polyornithine.

2. The metal nanocomposite of claim 1, wherein the one or more cationic and hydrophilic polymers enclose at least partially the hydrophobic surface.

3. The metal nanocomposite of claim 1, wherein the one or more metal nanoparticles have an average diameter of about 1 nm to about 1,000 nm.

4. The metal nanocomposite of claim 1, wherein the one or more cationic and hydrophilic polymers form a shell that has an average thickness of about 1 nm to about 40 nm.

5. The metal nanocomposite of claim 1, wherein the at least one organic surfactant is selected from the group consisting of: an alkyl trimethylammonium halide; a saturated fatty acid; an unsaturated fatty acid; a trialkylphosphine; a trialkylphosphine oxide; an alkylamine; an alkyl thiol; a sodium alkyl sulfate; and a sodium alkylphosphate.

6. The metal nanocomposite of claim 5, wherein the at least one organic surfactant is selected from the group consisting of: oleic acid; lauric acid; dodecylic acid; and dodecyl amine.

7. The metal nanocomposite of claim 1, wherein the one or more cationic and hydrophilic polymers have an average molecular weight (Mw) of about 1,000 to about 1,000,000.

8. The metal nanocomposite of claim 7, wherein the one or more cationic and hydrophilic polymers have a weight average molecular weight (Mw) of about 2,000 to about 30,000.

9. The metal nanocomposite of claim 1, wherein the one or more cationic and hydrophilic polymers are bound to an active substance selected from the group consisting of: a cell; an antigen; an antibody; a nucleic acid; a polypeptide; an organic fluorescent material; a carbohydrate; a lipid; a tumor marker-specific binding material; and a pharmaceutically active ingredient.

10. The metal nanocomposite of claim 9, wherein the active substance is bound to one or more amine groups of the one or more cationic and hydrophilic polymers.

11. The metal nanocomposite of claim 9, wherein the nucleic acid comprises DNA or RNA.

12. The metal nanocomposite of claim 9, wherein the organic fluorescent material comprises RITC (rhodamin A isothiocyanate) or FITC (fluorescein isothiocyanate).

13. The metal nanocomposite of claim 9, wherein the tumor marker-specific binding material comprises one or more materials selected from the group consisting of: phosphatidylserine; VEGFR; an integrin receptor; a Tie2 receptor; a somatostatin receptor; a vasointestinal peptide receptor; Herceptin; Rituxan; and folic acid.

14. The metal nanocomposite of claim 9, wherein the pharmaceutically active ingredient comprises one or more agents selected from the group consisting of: an anticancer agent; an antibiotic; a hormone; a hormone antagonist; an interleukin; an interferon; a growth factor; a tumor necrosis factor; an endotoxin; a lymphotoxin; a eurokinase; a streptokinase; a tissue plasminogen activator; a protease inhibitor; an alkylphosphocholine; a radioisotope labeled component; a surfactant; a cardiovascular system drug; a gastrointestinal system drug; and a nervous system drug.

15. The metal nanocomposite of claim 1, wrein the one or more cationic and hydrophilic polymers is polyethyleneimine.

16. A contrast composition comprising the metal nanocomposite of claim 1 and a pharmaceutically acceptable carrier or excipient.

17. A diagnosis composition comprising the metal nanocomposite of claim 1 and a pharmaceutically acceptable carrier or excipient.

18. The diagnosis composition of claim 17, wherein the one or more cationic and hydrophilic polymers in the metal nanocomposite are bound to an active substance selected from the group consisting of: a cell; an antigen; an antibody; a nucleic acid; a polypeptide; an organic fluorescent material; a carbohydrate; a lipid; a tumor marker-specific binding material; and a pharmaceutically active ingredient.

19. A pharmaceutical composition comprising the metal nanocomposite of claim 1 and a pharmaceutically acceptable carrier.

20. A method for preparing a metal nanocomposite of claim 1 comprising:
providing an aqueous solution containing one or more cationic and hydrophilic polymers to an organic solution containing one or more metal nanoparticles having hydrophobic surface, to form an emulsion; and
removing the organic solvent from the emulsion to form a metal nanocomposite preparation;
wherein:
the one or more metal nanoparticles is $MnFe_2O_4$;
the hydrophobic surface contains an organic surfactant having one or more hydrophobic moieties; and
the one or more cationic and hydrophilic polymers are selected from the group consisting of: polyethyleneimine, polyarcylamide, and polyornithine.

21. The method of claim 20, wherein the method further comprises binding the cationic and hydrophilic polymer with an active substance selected from the group consisting of: a cell; an antigen; an antibody; a nucleic acid; a polypeptide; an organic fluorescent material; a carbohydrate; a lipid; a tumor marker-specific binding material; and a pharmaceutically active ingredient.

22. The method of claim 20, wherein the method further comprises performing a thermal decomposition reaction of a hydrophobic surface stabilizer and a precursor of the metal nanoparticle in a solvent to form the one or more metal nanoparticles having a hydrophobic surface.

23. The method of claim 22, wherein the precursor comprises a metal carbonyl compound or a metal acetylacetonate compound.

24. The method of claim 20, wherein the organic solution comprises one or more solvents selected from the group consisting of: hexane; chloroform; benzene; diethylether; ethyl acetate; and dichloromethane.

25. The method of claim 20, wherein the aqueous solution comprises one or more solvents selected from the group consisting of: water; PBS; alcohol; and dimethylsulfoxide.

26. The method of claim 20, wherein the emulsion is formed under ultrasonication.

27. The method of claim 20, wherein the organic solvent is removed by evaporation.

28. A method for using a contrast composition to image the cells or tissues of a subject, the method comprising:
(a) administering an effective amount of a contrast composition comprising the metal nanocomposite of claim 1 and a pharmaceutically acceptable carrier or excipient to a subject; and
(b) detecting a signal emitted by the metal nanocomposite from the subject to obtain images of the cells or tissues of the subject.

29. A method for diagnosing a medical condition, the method comprising:
(a) administering an effective amount of a diagnosis composition comprising the metal nanocomposite of claim 1 and a pharmaceutically acceptable carrier or excipient to a subject; and
(b) detecting a signal emitted by the metal nanocomposite from the subject to obtain images, wherein the image is compared to a reference standard in order to diagnose the medical condition in the subject.

30. A method for simultaneously diagnosing and treating a medical condition, the method comprising:
(a) administering a therapeutically effective amount of a pharmaceutical composition comprising the metal nanocomposite of claim 1 and a pharmaceutically acceptable carrier or excipient to a subject, wherein the pharmaceutical composition is bound to an active substance; and
(b) detecting a signal emitted by the metal nanocomposite from the subject to obtain an image, wherein the image is compared to a reference standard in order to diagnose the medical condition in the subject and the active substance treats the medical condition in the subject.

* * * * *

UNITED STATES PATENT AND TRADEMARK OFFICE
CERTIFICATE OF CORRECTION

PATENT NO. : 8,916,134 B2  
APPLICATION NO. : 12/171812  
DATED : December 23, 2014  
INVENTOR(S) : Haam et al.

It is certified that error appears in the above-identified patent and that said Letters Patent is hereby corrected as shown below:

On the Title Page, Item (52), under "U.S. Cl.", in Column 1, Line 16,
delete "1/0018 (2013.01)" and insert -- 1/0018 (2013.01); B22F 9/24 (2013.01) --, therefor.

In the Drawings

On Sheet 3 of 7, replace Figs. 2A, 2B & 2C with the enclosed Replacement sheet.

In the Specification

In Column 1, Line 63, delete "(rhodamin" and insert -- (rhodamine --, therefor.

In Column 2, Line 6, delete "factor," and insert -- factor; --, therefor.

In Column 4, Line 55, delete "van de" and insert -- van der --, therefor.

In Column 8, Line 63, delete "intraoccularly," and insert -- intraocularly, --, therefor.

In Column 14, Line 19, delete "isothiocanate" and insert -- isothiocyanate --, therefor.

In Column 17, Line 65, delete "B."." and insert -- B." --, therefor.

In the Claims

In Column 19, Line 10, in Claim 12, delete "(rhodamin" and insert -- (rhodamine --, therefor.

In Column 19, Line 28, in Claim 15, delete "whrein" and insert -- wherein --, therefor.

Signed and Sealed this  
Twenty-first Day of July, 2015

Michelle K. Lee  
*Director of the United States Patent and Trademark Office*

CERTIFICATE OF CORRECTION (continued)
U.S. Pat. No. 8,916,134 B2

In Column 19, Line 51, in Claim 20, delete "having" and insert -- having a --, therefor.

In Column 19, Line 61, in Claim 20, delete "polyarcylamide," and insert -- polyacrylamide, --, therefor.